United States Patent
Fung et al.

(10) Patent No.: US 7,351,287 B2
(45) Date of Patent: Apr. 1, 2008

(54) METHOD AND APPARATUS FOR APPLYING PARTICULATE MATERIAL TO A SUBSTRATE

(75) Inventors: Paul Y. Fung, South River, NJ (US); Denis Tremblay, Quebec (CA)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 11/471,952

(22) Filed: Jun. 21, 2006

(65) Prior Publication Data

US 2006/0236930 A1 Oct. 26, 2006

Related U.S. Application Data

(62) Division of application No. 11/054,842, filed on Feb. 10, 2005, now Pat. No. 7,235,278.
(60) Provisional application No. 60/557,933, filed on Mar. 31, 2004.

(51) Int. Cl.
*B05C 19/02* (2006.01)
(52) U.S. Cl. ............... 118/308; 118/309; 118/DIG. 5; 156/578
(58) Field of Classification Search ............. 118/308, 118/309, DIG. 5; 427/182, 207.1, 208, 459, 427/2.15; 156/578
See application file for complete search history.

(56) References Cited

U.S. PATENT DOCUMENTS

| | | | | | |
|---|---|---|---|---|---|
| 2,811,130 | A | * | 10/1957 | Friderici | 118/701 |
| 2,841,516 | A | * | 7/1958 | Morton | 156/148 |
| 3,197,324 | A | * | 7/1965 | Brooks | 427/185 |
| 3,235,972 | A | * | 2/1966 | Hood et al. | 34/344 |
| 5,061,519 | A | * | 10/1991 | Long | 427/207.1 |
| 5,891,515 | A | * | 4/1999 | Dutheil et al. | 427/185 |
| 6,294,222 | B1 | * | 9/2001 | Cohen et al. | 427/459 |
| 6,355,309 | B1 | * | 3/2002 | Fleming et al. | 427/461 |

FOREIGN PATENT DOCUMENTS

| | | | |
|---|---|---|---|
| GB | 842950 | * | 7/1960 |
| GB | 993566 | * | 5/1965 |
| JP | 10-204384 | * | 4/1998 |
| WO | WO02/066088 | * | 8/2002 |

* cited by examiner

*Primary Examiner*—Laura Edwards

(57) ABSTRACT

A method and apparatus of applying a particulate material to a substrate includes applying adhesive to the substrate and passing the substrate through a chamber in which a particulate material is suspended in a fluid in order to adhere the particulate material to the substrate.

16 Claims, 5 Drawing Sheets

METHOD AND APPARATUS FOR APPLYING PARTICULATE MATERIAL TO A SUBSTRATE

CROSS-REFERENCE TO RELATED APPLICATIONS

The present application is a divisional application of U.S. patent application Ser. No. 11/054,842 filed on Feb. 10, 2005, now U.S. Pat. No. 7,235,278 which in turn claims priority to Provisional Patent Application No. 60/557,933 filed on Mar. 31, 2004, priority of both these applications is hereby claimed.

BACKGROUND OF THE INVENTION

1. Field of the Invention

The present invention generally relates to a method and apparatus for applying a particulate material to a substrate and, more particularly, to a fluidized bed apparatus and method of using such apparatus for applying a particulate material to a substrate.

2. Background of the Related Art

Application of materials to a substrate is commonly performed in order to manipulate various mechanical, chemical, physio-chemical, and/or electronic properties of the substrate. Particulate materials such as powders and fibers represent forms of material that may be applied to a substrate in order to modify the properties thereof. For example, metal substrates may be coated with powdered organic resins. Upon application of sufficiently high temperatures, the resinous particles melt and fuse on the surface of the metal substrate to form a continuous coating that enhances the chemical resistance of the metal substrate.

Particulate materials may also be applied to fibrous substrates, such as aggregations of non-woven and synthetic fibers. The particulate may thereby become enmeshed within the fibrous aggregate. Substrates treated in this way may be used to form absorbent articles including feminine hygiene articles such as sanitary napkins, tampons, and panty liners, as well as diapers and incontinence articles. During the manufacture of such articles, a fluid-absorbing powder (e.g. a superabsorbent powder) is applied to a moving fibrous substrate. The superabsorbent powder is thereby transferred to the surface of the fibrous material or regions within the fibrous material, thus enhancing the absorbent properties of the fibrous substrate.

The application of particulate materials to a substrate may be accomplished by any one of a number of know conventional means. For example, particulates may be applied using mechanical delivery devices such as conduits, nozzle sprayers, and the like.

Unfortunately, using conduits, nozzles, and the like to deliver particulate material to a substrate, particularly a substrate moving at a high speed, is subject to variety of problems. For example, it is difficult to apply the particulate material to a pre-determined, localized area of the substrate. In particular, if the spraying of the powder is not initiated and terminated within a tightly defined time interval, the particulate may be delivered to undesired locations rather than the desired location on the substrate. Furthermore, the particulate material is often subject to spreading, i.e., the particulate does not remain localized on the substrate and the particulate may migrate to locations where it is not desired, thereby contaminating the process. The above problems are compounded for substrates, including fibrous substrates, which are often processed at line speeds that are fast enough to promote scattering of the particulate to undesired locations on the substrate. Therefore, a need exists for a method and apparatus for applying a particulate material to a substrate that overcomes one or more of the above-mentioned drawbacks.

SUMMARY OF THE INVENTION

In view of the foregoing, a first aspect of the invention provides a method of applying a particulate material to a substrate, the method including the steps of applying an adhesive to a surface of the substrate, suspending a particulate material within a chamber and conveying the substrate through the chamber to thereby adhere the particulate material to the surface of the substrate.

A second aspect of the present invention provides a method of applying a particulate material to an article of manufacture, the method including the steps of applying adhesive to a surface of a layer that forms at least a part of an article of manufacture, suspending a particulate material within a chamber, conveying the article of manufacture through the chamber to thereby adhere the particulate material to the surface of the layer.

BRIEF DESCRIPTION OF THE DRAWINGS

A more detailed description of the invention is provided below, with reference to the appended drawings in which.

DETAILED DESCRIPTION

Figure 1:
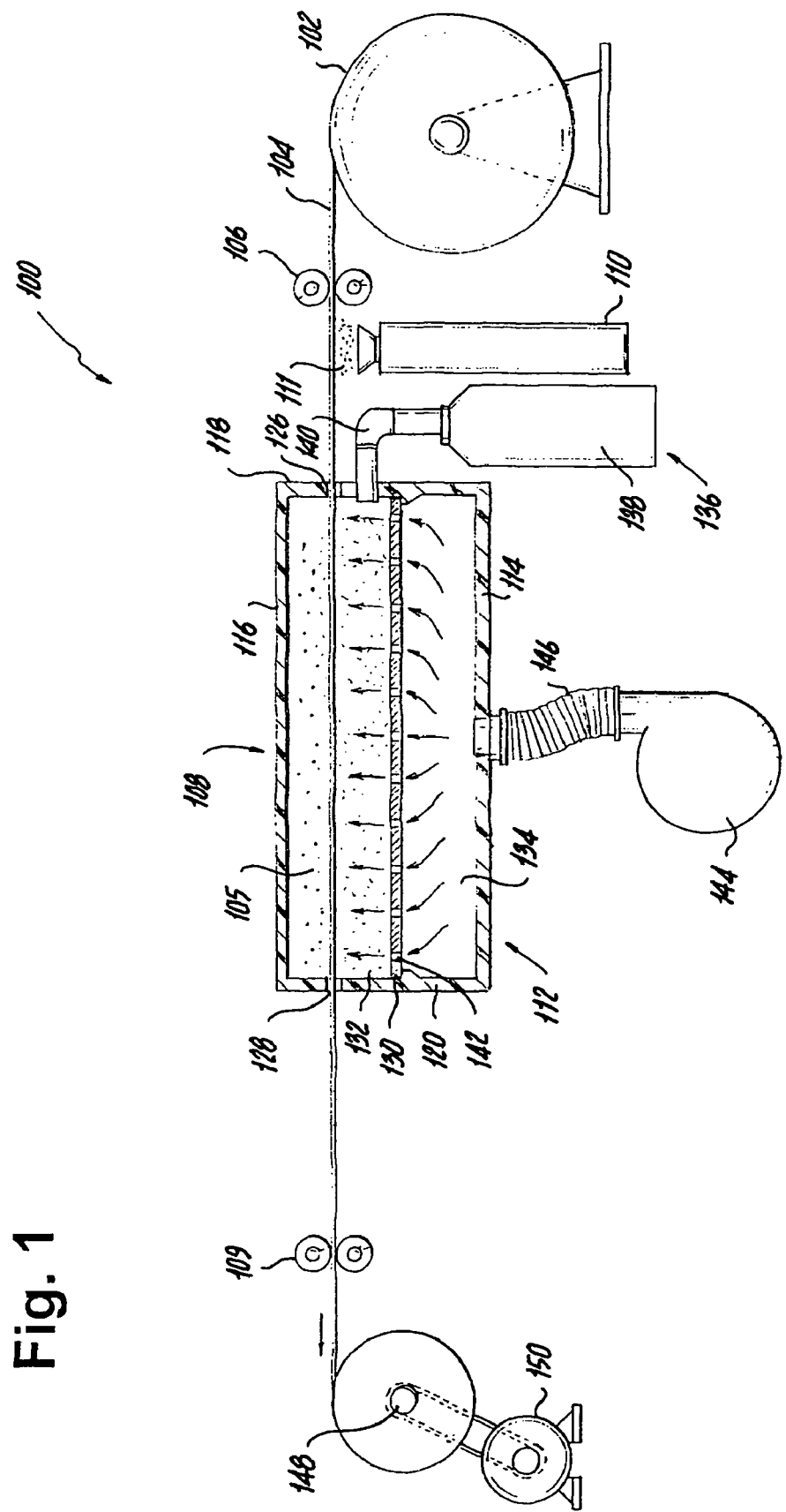
FIG. 1 is a schematic view of a particulate applicator apparatus according to a first embodiment of the present invention.
Figure 1A:
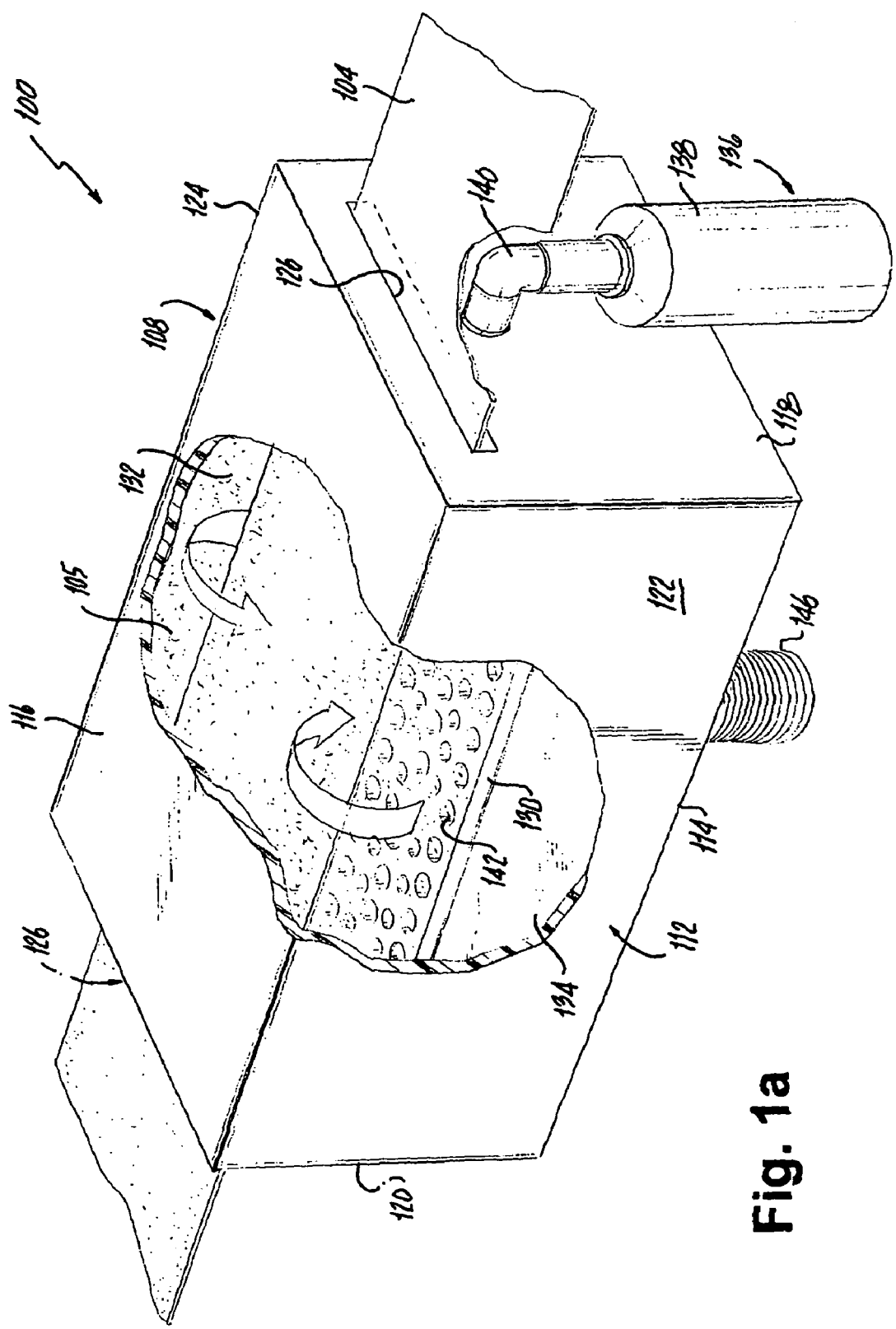
FIG. 1a is a detailed perspective view of the particulate applicator apparatus shown in FIG. 1 with a portion thereof cut away to reveal the interior of the apparatus.

Referring now to the drawings, wherein like reference numerals designate corresponding structure throughout the views, and referring in particular to FIGS. 1 and 1a, a particulate applicator apparatus according to first embodiment of the present invention is generally identified by the reference numeral 100. In the apparatus 100, a substrate 104 is taken from a supply roll 102 and conveyed in a machine direction by a pair of driven nip rolls 106. The driven nip rolls 106 cooperate with a second pair of nip rolls 109 to regulate the tension of the substrate and convey the substrate 104 through a particulate suspension assembly 108.

The substrate 104 passes, from the first pair of nip rolls 106, in proximity to an adhesive applicator 110 for applying an adhesive 111 to a surface of the substrate 104. In the embodiment shown in FIG. 1, the adhesive 111 is applied to a bottom surface of the web. However, it is understood that the adhesive 111 could alternatively be applied to a top surface of the substrate 104 or to both the top and bottom surfaces of the substrate 104. As shown, the adhesive applicator 110 is arranged upstream relative to the particulate suspension assembly 108 so that the adhesive 111 is applied to the substrate 104 prior to the entry of the substrate 104 into the particulate suspension assembly 108.

After the adhesive 111 is applied to a surface of the substrate 104, the substrate 104 is conveyed into and through the particulate suspension assembly 108. The particulate suspension assembly 108 is generally defined by a substantially enclosed chamber 112 including a bottom wall 114; an opposed top wall 116 arranged in spaced relationship relative to the bottom wall 114; a pair of opposed end walls 118 and 120 arranged in spaced relationship to one another, the end walls 118 and 120 extending from the bottom wall 114 to the top wall 116; and a pair of opposed side walls 122 and 124 arranged in spaced relationship to one another.

The end wall 118 includes a port 126 to permit the entry of the substrate 104 into the particulate suspension assembly 108 and the end wall 120 includes a corresponding port 128 to permit the substrate 104 to exit the particulate suspension assembly 108.

As shown in FIG. 1a the end walls 118 and 120 each have a length that is longer than a width of the substrate 104. In this manner, as shown, the particulate material 105 is free to pass from a position below the substrate, between the terminal side edges of the substrate 104 and the side walls 122 and 124, and above substrate 104. Thus, the particulate material 105 may freely pass from a position below the substrate 104 to a position above the substrate 104.

Arranged within the chamber 112 is a particulate support surface 130 that separates a particle impregnated chamber 132 from an air plenum chamber 134. The particulate support surface 130 extends from end wall 118 to the end wall 120 in first direction and from the side wall 122 to side wall 124 in a second direction.

The particulate support surface 130 is a horizontal planar member that is structured and arranged such that when the particulate material 105 is not in a suspended state the particulate material 105 may be allowed to fall (e.g. through gravitational forces) such that the particulate material 105 rests on the particulate support surface 130.

The apparatus 100 also includes a particulate delivery system 136 for delivering the particulate material 105 to the chamber 132. The particulate delivery system 136 generally includes a hopper 138 for storing the particulate material 105 and a particulate delivery tube 140 coupled to the hopper 138 for transporting the particulate material 105 to the chamber 132. The particulate delivery system 136 may include a valve or the like for enabling the selective metering of the particulate material 105 into the chamber 132. The particulate delivery system 136 may be arranged as a simple gravity fed system, i.e. such that when the valve is opened the particulate passes from the hopper 138 through the particulate delivery tube 140 and into the chamber 132. Preferably, the particulate delivery system 136 includes a variable feed that is coordinated with the use of the particulate 105 such that the particulate 105 within the chamber 132 is automatically replenished. Other suitable methods of introducing the particulate into the chamber 132 may of course also be used and should be considered within the scope of the present invention.

The particulate support surface 130 includes a plurality of pores 142 (shown exaggerated in size in the figures for clarity) formed therethrough in order to permit the flow of a pressurized fluid from the air plenum chamber 134 into the chamber 132. A pressurized fluid is delivered from a fluid source 144 through a fluid delivery tube 146 and into air plenum chamber 134. The pressurized fluid then passes in a uniform manner through the pores 142 in the particulate support surface 130 and into the chamber volume 132. The delivery of the pressurized fluid into the chamber 132 functions to suspend the particulate material 105 within the chamber 132.

The pressurized fluid is preferably selected such that it is a fluid that is chemically inert to the particulate material 105 and the substrate 104 at the temperature and pressure in which the process is performed. The fluid may be a gas, and may comprise, for example, nitrogen, air, or similar gases that fulfill the requirements specified above.

Furthermore, the relative humidity of the fluid may be adjusted if necessary. For example, if the particulate material 105 is capable of absorbing water vapor, the relatively humidity of the fluid may be maintained at a low level to prevent the particulate material 105 from absorbing an appreciable amount of water vapor. The fluid is introduced into the chamber volume 132 at a flow rate such that the particulate material 105 is substantially uniformly suspended within the chamber volume 132.

During operation of the apparatus 100 shown in FIG. 1, the adhesive 111 is applied to the substrate 104 and the substrate is conveyed through the particulate suspension assembly 108 while the particulate 105 is maintained within a suspended state in chamber volume 132. As the substrate 105 passes between ports 126 and 128 of the particulate suspension assembly 108, the substrate 104 having the adhesive 111 disposed thereon, is exposed to the particulate material 105 suspended in the chamber volume 132. During this period of exposure, the particulate material 108 sticks to, joins or otherwise associates with the substrate 104 via the adhesive 111.

The time of exposure of the adhesive 111 disposed on the surface of the substrate 104 to the suspended particulate material 105 within chamber 132 is related to the speed at which the substrate 142 travels as it passes through chamber 132 as well as the length of the path that the substrate 104 travels between ports 126 and 128. The substrate 104 may, for example, be moved during this time period at a rate from about 200 feet per minute to about 1500 feet per minute.

The adhesive 111 applied to the surface of the substrate 104 is preferably exposed to the particulate material 105 for a time period that is sufficient to passivate the adhesive. The adhesive 111 becomes passivated when the adhesive 111 has been exposed to sufficient particulate material 105 such that the adhesive 111 is rendered substantially non-tacky.

After the particulate material 105 has been applied to the substrate 104 within the particulate suspension assembly 108, the coated substrate 104 exits the particulate suspension assembly 108 via port 128. The coated substrate 104 is then conveyed to a rewind reel 148. The rewind reel 148 may be powered by a drive motor 150. Air jets (not shown in the Figures) or the like may be arranged at the ports 126 to assist in maintaining the particulate material 105 within the chamber 132 and thereby preventing the unintended escape of the particulate material from the chamber. Moreover, an air jet or the like may be arranged at port 128 which is directed at the surface of the web. Such an air jet would serve to remove any excess particulate that has not securely adhered to the surface of the substrate 104.

In the embodiment of the invention shown in FIG. 1, the substrate 104 is a continuous element such as a relatively long and thin sheet of fibrous material. Examples of continuous substrates that may be processed using embodiments described herein include webs of woven or non-woven fibrous material, apertured films, plastic substrates, layered film structures, laminated and/or composite materials, among other continuous substrates that may be formed by the interlocking or laying of fibers, lamination, extrusion, calendaring, or combinations of these processes. The substrate 104 may have varying regular or irregular cross-sectional shapes, such as sheets, threads, films, and the like. The substrate 104 may have pores of varying sizes, shapes, or distributions.

The adhesive 111 that is applied to the substrate 104 may be of varying compositions. The composition of the adhesive 111 is generally selected so as to facilitate the joining of the selected particulate material 105 to the substrate 104. The adhesive 111 is generally a tacky composition that is selected to chemically and/or mechanically bond the particulate material 105 to the substrate 104 via such mechanisms as van der Waals forces, hydrogen bonding, dipole forces, and the like. In one embodiment of the invention, the adhesive 111 comprises a thermoplastic compound such as various polymers or co-polymers of styrene, ethylene, vinyl acetate, as well as copolymers of various organic materials that are selected to provide appropriate melt viscosity, bond-strength, and processibility. The thermoplastic polymer may be combined with various tackifying resins, plasticizers, antioxidants and other functional ingredients such as are used in typical hot-melt adhesive formulations for adhering various materials to plastics, fibers, and other organic materials.

While the adhesive 111 is generally selected to facilitate the incorporation of the particulate material 104 onto or into the substrate 104, the composition of the adhesive 111 may be selected at least partly based upon other functional criteria. For example, the adhesive may be selected to deliver certain mechanical, electrical, optical, chemical, fluid-absorptive, sensory, or other properties.

In one embodiment of the invention, the composition of the adhesive 111 is selected to tackily adhere a flavor or calcium-containing, particulate to a polymeric dental floss substrate 104. The dental floss substrate 104 may be coated with a substance such as a wax that may be rendered tacky through various means including heating. The tacky substance thereby serves as the adhesive 111 for adhering the particulate material 105 thereto.

The particulate material 105 to be applied to the substrate 104 may be any finely divided matter in a solid state, such as powders, fibers, and combinations thereof, that may be suspended in the chamber 132. The powders and fibers that may comprise the particulate material 105 may be organic or inorganic materials. The particulate material 105 may have a wide range of densities, particle sizes, porosities, and chemical compositions.

In one embodiment of the invention, the particulate material 105 is a liquid-absorbing polymer, such as a superabsorbent polymer. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. One suitable example of superabsorbent particles is AQUAKEEP SA-70, commercially available from Sumitomo Seika Chemicals Co., Ltd.

The adhesive applicator 110 that is used to apply the adhesive 111 to the substrate 104 may be, for example, a conventional hot-melt adhesive applicator such as a slot coater, a swirl-spray applicator, or a rotary screen applicator. The adhesive applicator 110 may include nozzles or apertures of varying dimensions to permit the transfer of adhesive 111 onto the substrate 104. The adhesive applicator 110 may be structured and arranged to coat the entire surface of the substrate 104 so that the entire surface of the substrate is coated with particulate material 105. Alternatively, the adhesive applicator 110 may be structured and arranged so that the adhesive 111 is applied to the substrate in a selected pattern so that particulate material 105 adheres to the substrate in a corresponding pattern.

Unlike fluidized bed apparatuses used for coating small substrates that typically include electrodes for electrostatically charging the particulate material to be applied to the substrate, the apparatus of present invention preferably does not include any means to charge the particulate material 105. By excluding electrodes, it is believed that the adhesive 111 may be covered with a layer of the particulate material 105 that is relatively thick as compared to that achieved by prior art devices. For example, the thickness of the layer of particulate material 105 adhered to the substrate 104 may be in the range from about 0.1 millimeter to about 1 millimeter.

Figure 2:
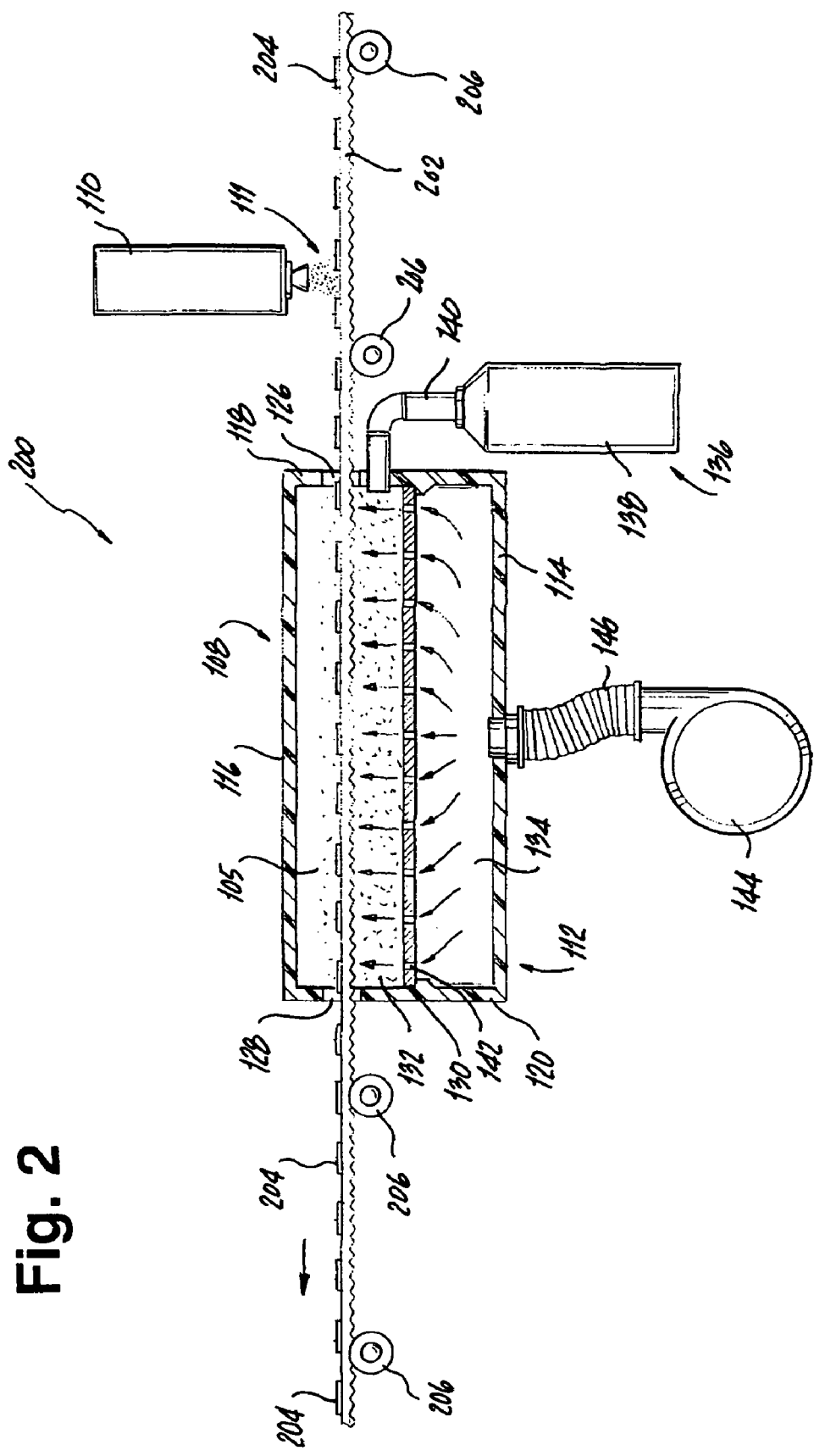
FIG. 2 is a schematic view a particulate applicator apparatus according to a second embodiment of the present invention.

Reference is now made to FIG. 2, in which a particulate applicator apparatus 200 according to second embodiment of the present invention is depicted. The apparatus 200 is similar in construction to the apparatus 100 shown in FIG. 1 and described above. However, the apparatus 200 is structured to convey a belt 202 having a plurality of articles 204 arranged thereon in a machine direction. The apparatus 200 includes a plurality of drive rollers 206 that are structured and arranged to engage and convey the belt 202 in the machine direction. Drive rollers 206 of the type employed herein may be of any conventional construction. Such drive rollers 206 are well known in the art and are well known to those skilled in the art and thus are not described in detail herein. The adhesive applicator 110 is arranged to apply an adhesive 111 to an exposed upper surface of the article 204. After the adhesive 111 is applied to the exposed upper surface of the article 204, the article 204 is conveyed on the belt 202 into and through the particulate suspension assembly 108 to thereby adhere the particulate 105 to the upper surface of the article 204. After the article 204 passes through particulate suspension assembly 108 the article may be conveyed further in the machine direction so that the article 204 may further processed.

In the embodiment of the invention depicted in FIG. 2, the article 204 is preferably a sanitary protection article such a sanitary napkin or panty liner and the apparatus 200 is preferably is incorporated within a machine for manufacturing such an article. The adhesive 111 and particulate material 105 may be applied to any appropriate constituent layer of the sanitary protection article, such as the backing layer, absorbent core, transfer layer, or cover layer.

Figure 3:
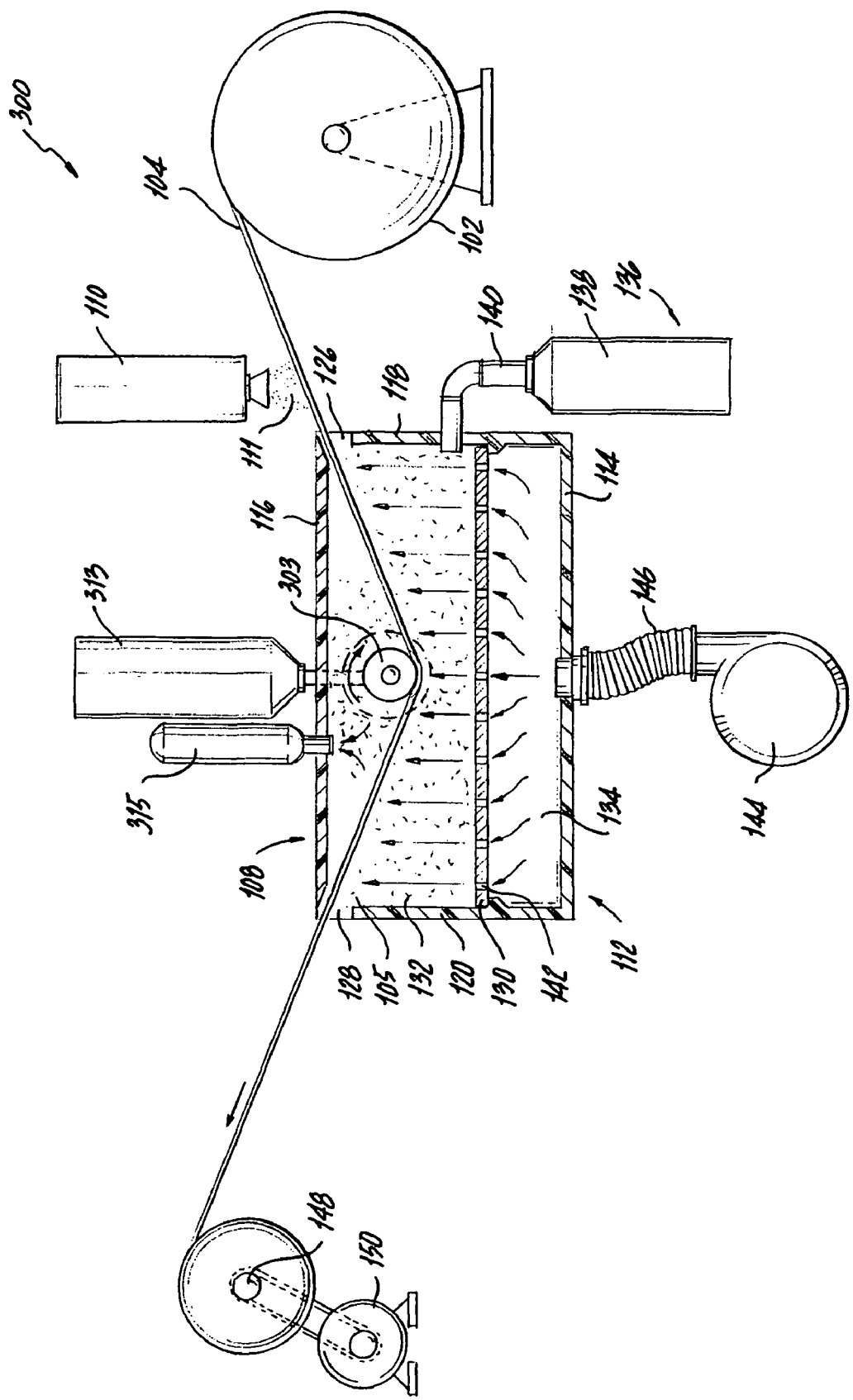
FIG. 3 is a schematic view of a particulate applicator apparatus according to a third embodiment of the present invention.
Figure 4:
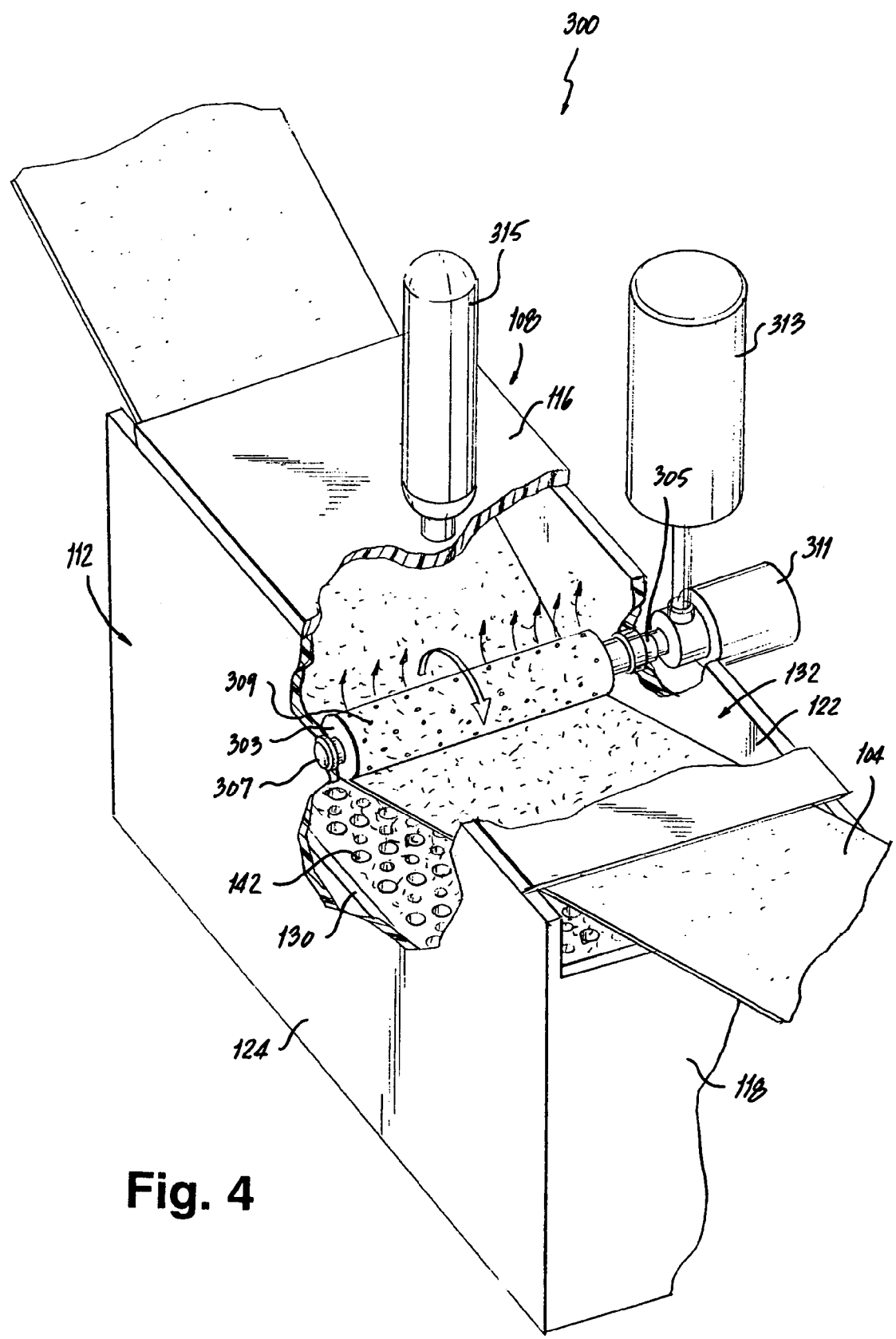
FIG. 4 is a detailed perspective view of the particulate applicator apparatus shown in FIG. 2 with a portion thereof cut away to reveal the interior of the apparatus.

Reference is now made to FIGS. 3 and 4, in which a particulate applicator apparatus 300 according to third embodiment of the present invention is depicted. The apparatus 300 is structured to convey a continuous substrate 104 from a supply roll 102, through the particulate suspension assembly 108, to a rewind reel 148. Although not shown in FIG. 3, the apparatus 300 may include driven nip rollers as shown in FIG. 1, to regulate the tension of the substrate 104 and convey the substrate through the particulate suspension assembly 108. In the embodiment of the invention shown in FIG. 3, the adhesive applicator 110 is arranged to apply the adhesive 111 to a top surface of substrate 104.

Apparatus 300 further includes a guide roll 303 that is arranged within the particulate suspension assembly 108 and is adapted to guide the substrate 104 along a descending path as the substrate 104 enters the particulate suspension assembly 108 and a ascending path as the substrate exits the particulate suspension assembly 108. The guide roll may be mounted to opposed side walls 122 and 124 of the chamber 112. Alternatively, as shown in FIG. 4, the side walls 122 and 124 may be structured to permit the passage of mounting shafts 305 and 307 through the side walls 122 and 124 to thereby permit the shafts 305 and 307 to be mounted to a journal box or the like. The guide roll 303 may be structured as a idler roll, or in the alternative, as show in FIG. 4, the guide roll 303 may be coupled to a drive motor 311 adapted to rotate roll 303.

It has been discovered that when the apparatus according to the present invention is used apply a particulate material to substrate having a wide transverse length (i.e. a longer width) it may be desirable to introduce a second flow of pressurized fluid into the particulate suspension assembly 108 at a location above the substrate 104. In this way, a first flow of pressurized fluid is introduced from beneath the substrate, and a second flow of pressurized fluid is introduced from above the substrate, to thereby promote the uniform dispersion of the particulate material 105 throughout the chamber 132. The introduction of the second flow of pressurized fluid into the particulate suspension assembly 108 may be accomplished in a numbers of ways. According to a preferred embodiment of the present invention shown in FIG. 4, the guide roll 303 is structured so that a surface thereof includes a plurality of pores 309 to permit the passage of a second flow of pressurized fluid through the guide roll 303 and into the chamber 132. The guide roll 303 is operably coupled to a fluid source 313 for delivering a pressurized fluid to the guide roll 303.

The particulate applicator apparatus 300 further includes a vacuum tube 315 or the like that is structured and arranged to communicate with the chamber 132. The vacuum tube 315 is adapted to apply a vacuum to the chamber 132 to promote the suspension of the particulate material within the chamber 132. In addition, the vacuum applied by the vacuum tube 315 helps maintain the particulate material 105 within the chamber so that the particulate material does not escape from the chamber 132 via ports 126 and 126. The vacuum tube 315 is preferably provided with a filter or the like at its communication point with the chamber 132, the filter being structured and arranged to prevent the particulate material 105 from being removed from the chamber 132 by the vacuum applied through the vacuum tube 315.

Although the embodiments of the invention depicted in the Figures have shown particulate suspension assembly 108 having a horizontal configuration, i.e. so that the substrate is conveyed through the particulate suspension assembly 108 along a horizontal path or a declining and inclining path, it is possible that the particulate suspension assembly 108 could be arranged in a vertical fashion. In such a configuration, the particulate suspension assembly 108 is arranged in vertical configuration and the substrate 104 is introduced into a bottom portion of the assembly and then conveyed in vertical direction through the assembly 108.

EXAMPLE

A laboratory model of the present invention was constructed according to the embodiment of the invention shown in FIG. 3. The particulate suspension assembly 108 was constructed from a thermoplastic material, commercially available as LEXAN®, manufactured by the GE Plastics. The bottom wall 114 and opposed top wall 116 had dimensions of 14"×14" (L×W) and a thickness of 0.500". Each side wall 118 and 120 had dimensions of 14"×14" and a thickness of 0.500". The substrate 104 passed along a descending and ascending path of the type shown in FIG. 3.

The descending angle of approach of the substrate 104 to the porous roll 303 arranged within the particulate suspension assembly 108 was 5° relative to the horizontal plane defined at the tangential point of contact between the substrate 104 and the porous roll 303 and the ascending angle of egress of the substrate was 5°. Thus, the total length of the path traveled by the substrate within the chamber was approximately 86".

The substrate 104 was a polyethylene film, commercially available as PLIANT 3492A, from Pliant Corp. The substrate was conveyed at a speed of 40 ft/min through the particulate suspension assembly 108.

A commercially available adhesive, FULLER HL 1042, from the Fuller Corp., was applied to an upper surface of film by a Meltex slot coating unit at a rate of 24 gsm. The slot coating unit was arranged 9 feet from the entry of the substrate into particulate suspension assembly 108, as measured from the point of application of the adhesive to the substrate to the entry point of the substrate into the particulate suspension assembly 108, along the path of the substrate.

The particulate material suspended within the particulate suspension assembly was a super absorbent polymer, AQUAKEEP SA-70, commercially available from Sumitomo Seika Chemicals Co., Ltd.

The particulate support surface 130 was constructed from fritted glass and had dimensions of 12"×12" (L×W) and a thickness of 0.325". The particulate support surface 130 included a plurality of pores formed there through, the pores being uniformly spaced from each other at a distance of 0.250" and having a diameter of 15 microns. The support surface 130 was arranged approximately 12" from the bottom wall 114, as measured from the top surface of the bottom wall 114 to the bottom surface of the support surface 130.

A pressurized flow of air was introduced into the bottom of particulate suspension assembly 108 through a fluid delivery tube 146. The air was introduced to the particulate suspension assembly at a pressure in the range of 5 to 10 psi.

A guide roll 303 was arranged within the particulate suspension assembly as shown in FIG. 3, the roll was constructed from a porous ceramic material of the type commercially available from Soilmoisture Equipment Corp. The ceramic material had a thickness of approximately 0.5" inches, an approximate porosity of 50% by volume and a maximum pore size of 6.0 μm. The roll was constructed to have a diameter of 1.5 inches as measured from the outer surface of the roll mantle. A pressurized air flow was introduced into the porous roll at a pressure of 5 psi.

The substrate was conveyed at a uniform speed of approximately 40 ft/min from the supply roll 102, past the adhesive applicator 110 and through the particulate suspension assembly 108.

Two air knives were positioned at the exit port of the particulate suspension assembly 108 delivered an air flow in a direction parallel to the path of travel of the web at a pressure of 15 psi.

After the substrate passed through the particulate suspension assembly 108, sections thereof were inspected and the particulate material was securely adhered to the substrate and the adhesive was substantially passivated, i.e. rendered substantially non-tacky.

Embodiments of the present invention are advantageous for applying a particulate material to a substrate in that the substrate can be brought into communication with a fluidized bed of particulate material and adhesive formed on the substrate holds the particulate material in place. The substrate may be conveyed at high speeds and the particulate material is transferred to the substrate in well-defined, pre-determined patterns. The use of a compensating fluid allows a secondary fluidized bed to encompass a shadow zone, thereby enhancing the application of the particulate material to the substrate. Mechanical supports such as tension rollers may be incorporated into the apparatus to promote the passivation of the adhesive and/or bonding the particulate firmly to the adhesive.

Embodiments of the invention are particularly advantageous for applying particulate forms of water-absorbing polymers such as polyacrylic acids, odor-control agents including zeolites, ethylenediaminetetraacetic acid (EDTA) to substrate materials. For example, such particulate material may be applied to fibrous liquid-absorbing or liquid-penetrating layers, fluid transfer layers, or plastic barrier films that are known in the art of manufacture of absorbent articles including sanitary napkins, pantilners, diapers, wound care articles, and the like. The process used herein can also be used to coat surgical masks, wipes, and other medical use articles where a selected property is to be imparted to substrate by application of a particulate material thereto.

Other functional particulate materials, such as nano particulates and in particular nanoclaves, may also be applied to substrate materials using the method according to the present invention. Likewise particulate materials that impart a particulate characteristic, such as a pigment, flavor or the like could also be selective be applied to material using the process disclosed herein.

While the foregoing is directed to various specific embodiments of the present invention, other further embodiments maybe devised without departing from the scope of the present invention.

What is claimed is:

1. An apparatus for applying a particulate material to a substrate, comprising:
    a particulate suspension assembly defining a chamber for suspending a particulate material within said particulate suspension assembly, said particulate suspension assembly having a first port and a second port;
    a conveyor structured and arranged for conveying a substrate into said chamber volume via said first port, through said chamber volume, and out of said chamber volume via said second port;
    a fluid delivery tube arranged in flow communication with said chamber for delivering a flow of pressurized fluid into said chamber for suspending a particulate material in said chamber, said pressurized fluid being introduced into said chamber at a selected pressure sufficient to suspend the particulate material within said chamber;
    an adhesive applicator for coating a surface of said substrate with an adhesive prior to the entry of said substrate into said chamber;
    a fluid source for delivering a second flow of pressurized fluid into said chamber;
    a porous roll arranged within said chamber, said porous roll having a plurality of pores in an surface thereof, wherein said porous roll is operably coupled to said fluid source for delivering a second flow of pressurized fluid, whereby said second flow of pressurized fluid is delivered into said porous roll and then said second flow of pressurized fluid passes through said pores of said porous roll into said chamber;
    whereby said adhesive is applied to said substrate and said coated substrate is conveyed through said chamber to thereby place said adhesive and said particulate material in communication to thereby adhere said particulate material to said substrate.

2. The apparatus according to claim 1, wherein said adhesive applicator is structured and arranged to apply said adhesive in a pre-determined pattern to the substrate.

3. The apparatus according to claim 1, wherein said particulate is selected from the group consisting of fibers, powders, and combinations thereof.

4. The apparatus according to claim 1, wherein said particulate is a super-absorbent polymer.

5. The apparatus according to claim 1, wherein said substrate comprises a web of fibrous material.

6. The apparatus according to claim 1, wherein the substrate has a thickness less than about 5 mm.

7. The apparatus according to claim 1, wherein said conveyor is structured and arranged to convey said substrate at a speed of about 200 feet per minute to about 1500 feet per minute.

8. The apparatus according to claim 7, wherein a length of a path of said substrate within said chamber and a speed of said substrate within said chamber are selected so that said adhesive is exposed to said particulate material for a sufficient length of time to passivate said adhesive.

9. The apparatus according to claim 1, wherein said fluid delivery tube is arranged in flow communication with said chamber at a location below said substrate.

10. The apparatus according to claim 1, wherein said porous roll is arranged in surface to surface contact with said substrate to thereby guide said substrate.

11. An apparatus for applying a particulate material to an article of manufacture, comprising:
    a particulate suspension assembly defining a chamber for suspending a particulate material within said particulate suspension assembly, said particulate suspension assembly having a first port and a second port;
    a belt for supporting a plurality of articles of manufacture;
    a conveyor structured and arranged for conveying said belt, with said articles of manufacture arranged thereon, into said chamber volume via said first port, through said chamber volume, and out of said chamber volume via said second port;
    a fluid delivery tube arranged in flow communication with said chamber for delivering a flow of pressurized fluid into said chamber for suspending a particulate material in said chamber, said pressurized fluid being introduced into said chamber at a selected pressure sufficient to suspend the particulate material within said chamber;
    an adhesive applicator for coating a surface of a layer that forms at least a part of said article of manufacture with an adhesive prior to the entry of said article of manufacture into said chamber;
    a fluid source for delivering a second flow of pressurized fluid into said chamber;
    a porous roll arranged within said chamber, said porous roll having a plurality of pores in an surface thereof, wherein said porous roll is operably coupled to said fluid source for delivering a second flow of pressurized fluid, whereby said second flow of pressurized fluid is delivered into said porous roll and then said second flow of pressurized fluid passes through said pores of said porous roll into said chamber;
    whereby said adhesive is applied to said layer and said coated article of manufacture is conveyed through said chamber to thereby place said adhesive and said particulate material in communication and thereby adhere said particulate material to said layer.

12. The apparatus according to claim 11, wherein said plurality of articles of manufacture comprise a plurality of sanitary protection articles.

13. The apparatus according to 11, wherein said layer of said article of manufacture is one of a backing layer, a transfer layer, cover layer or a layer of an absorbent core.

14. The apparatus according to claim 11, wherein said an adhesive applicator is structured and arranged to apply said adhesive in a pre-determined pattern.

15. The apparatus according to claim 11, wherein said particulate is selected from the group consisting of fibers, powders, and combinations thereof.

16. The apparatus according to claim 11, wherein said particulate is a super-absorbent polymer.

* * * * *